United States Patent
Bo et al.

(10) Patent No.: US 11,837,325 B2
(45) Date of Patent: Dec. 5, 2023

(54) METHOD FOR IDENTIFYING BALANCED TRANSLOCATION BREAK POINTS AND CARRYING STATE FOR BALANCED TRANSLOCATIONS IN EMBRYOS

(71) Applicant: YIKON GENOMICS (SHANGHAI) CO., LTD, Shanghai (CN)

(72) Inventors: Shiping Bo, Shanghai (CN); Zhen Zhang, Shanghai (CN); Jun Ren, Shanghai (CN); Yumei Gao, Shanghai (CN); Sijia Lu, Shanghai (CN)

(73) Assignee: YIKON GENOMICS (SHANGHAI) CO., LTD, Shanghai (CN)

( * ) Notice: Subject to any disclaimer, the term of this patent is extended or adjusted under 35 U.S.C. 154(b) by 1103 days.

(21) Appl. No.: 16/490,488

(22) PCT Filed: Mar. 2, 2018

(86) PCT No.: PCT/CN2018/077895
§ 371 (c)(1),
(2) Date: Aug. 30, 2019

(87) PCT Pub. No.: WO2018/157861
PCT Pub. Date: Sep. 7, 2018

(65) Prior Publication Data
US 2020/0010890 A1   Jan. 9, 2020

(30) Foreign Application Priority Data

Mar. 2, 2017 (CN) .......................... 201710119785.8

(51) Int. Cl.
G16B 20/20 (2019.01)
G16B 30/10 (2019.01)
G16B 25/20 (2019.01)
C12Q 1/6874 (2018.01)

(52) U.S. Cl.
CPC ........... *G16B 20/20* (2019.02); *C12Q 1/6874* (2013.01); *G16B 25/20* (2019.02); *G16B 30/10* (2019.02)

(58) Field of Classification Search
None
See application file for complete search history.

(56) References Cited

FOREIGN PATENT DOCUMENTS

| CN | 102171565 A | 8/2011 |
|---|---|---|
| CN | 105543339 A | 5/2016 |
| CN | 105574361 A | 5/2016 |
| CN | 105874082 A | 8/2016 |
| CN | 106834490 A | 6/2017 |
| WO | 2005007869 A2 | 1/2005 |
| WO | 2007070482 A3 | 6/2007 |

OTHER PUBLICATIONS

Voet et al. "Single-cell paired-end genome sequencing reveals structural variation per cell cycle." Nucleic Acids Research. 2013. vol. 41(12), pp. 6119-6138. (Year: 2013).*
Treff et al. "Routinely distinguishing normal and balanced translocation carrier embryos using SNP arrays." Fertility & Sterility. 2014. vol. 102(3), Supplement, e181, Abstract. (Year: 2014).*
Nilsen et al. "Copynumber: Efficient algorithms for single- and multi-track copy number segmentation." BMC Genomics. 2012. vol. 13(591), pp. 1-16. (Year: 2012).*
Sims et al. "Sequencing depth and coverage: key considerations in genomic analyses." Nature Reviews Genetics. 2014. vol. 15, pp. 121-132. (Year: 2014).*
Huang et al. "Single-Cell Whole-Genome Amplification and Sequencing: Methodology and Application." Annual Review of Genomics and Human Genetics. vol. 16, pp. 79-102. (Year: 2015).*
Cimadomo et al. "The Impact of Biopsy on Human Embryo Developmental Potential during Preimplantation Genetic Diagnosis." BioMed Research International. 2016. vol. 2016, pp. 1-10. (Year: 2016).*
Knott. "Quantitative EEG Methods and Measures in Human Psychopharmacological Research." Human Psychopharmacology: Clinical and Experimental. 2000. vol. 15, pp. 479-498. (Year: 2000).*
Chiang et al. "High-resolution mapping of copy-number alterations with massively parallel sequencing." Nature Methods, vol. 6(1), pp. 99-103. (Year: 2009).*
Zhang, Yanxia, Authorized Officer, State Intellectual Property Office of the P.R. China, "International Search Report" in connection with related International Application No. PCT/CN2018/077895, dated May 31, 2018, 4 pgs.

* cited by examiner

*Primary Examiner* — John S Brusca
*Assistant Examiner* — Steven W. Bailey
(74) *Attorney, Agent, or Firm* — Kolisch Hartwell, P.C.

(57) ABSTRACT

Provided is a method for identifying balanced translocation breakpoints and a carrying state for balanced translocations in embryos, comprising the following steps: amplifying and sequencing a sample; comparing the sequence which is obtained by means of sequencing with a reference genome and analyzing copy numbers; accurately determining the position of a translocation breakpoint; detecting single nucleotide polymorphisms (SNPs) around the breakpoint and genotyping the SNPs; analyzing an embryonic haplotype, and comprehensively determining a normal chromosome and a translocation chromosome haplotype; determining the embryonic carrying state and, according to the haplotype, selecting an embryo which does not carry a balanced translocation.

8 Claims, 1 Drawing Sheet

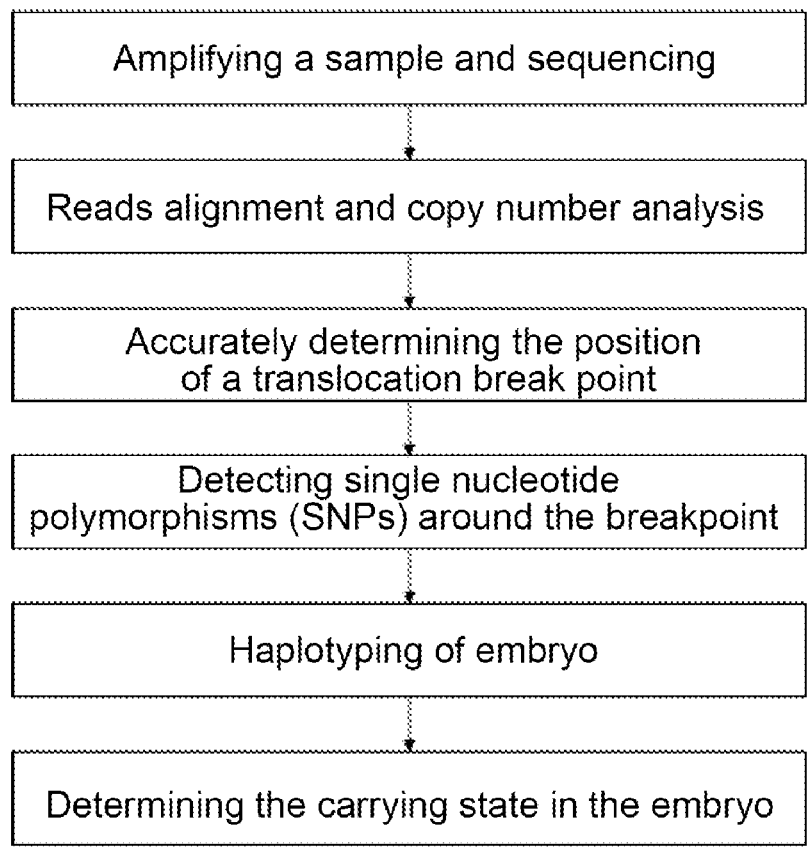

METHOD FOR IDENTIFYING BALANCED TRANSLOCATION BREAK POINTS AND CARRYING STATE FOR BALANCED TRANSLOCATIONS IN EMBRYOS

FIELD OF THE INVENTION

The present application relates to the field of biotechnology, particularly to the field of genome sequence analysis, and more particularly to methods for identifying a balanced translocation breakpoint and for determining a balanced translocation-carrying status in an embryo.

BACKGROUND OF THE INVENTION

In the fields of scientific researches and clinical applications involving biomedical sciences and reproductive genetics, balanced translocations are very common structural chromosomal abnormalities in neonates, and account for approximately 1/500-1/625 of neonates. Balanced translocation carriers usually have normal phenotypes, but some may suffer from diseases such as autism, intellectual disability, and congenital anomalies caused by genetic mutations such as microduplication, microdeletion, and genetic damage. Balanced translocation carriers are more likely to produce unbalanced gametes during reproduction, leading to habitual abortion and even infertility. Therefore, it is very necessary to select out and identify embryos that do not carry balanced translocations so as to block the transmission of balanced translocations from carriers to their offspring.

Current methods for identifying balanced translocations include Comparative Genomic Hybridization (CGH), Fluorescence in situ Hybridization (FISH), SNP array, MicroSeq-PGD, and other technologies.

However, Comparative Genomic Hybridization has limitations such as low resolution (in Mb level), low throughput, and high cost. Fluorescence in situ Hybridization is only for a specific position, and has low resolution and unstable probe hybridization efficiency. In addition, because balanced translocations involve almost every band of each chromosome, it is required to design individually a probe for each balanced translocation carrier, which is time consuming and costly, so that the Fluorescence in situ Hybridization is unsuitable for being used as a general detection technique. The SNP array is designed for the whole genome. Because the SNP distribution is not absolutely uniform, the effective loci available for linkage analysis around a balanced translocation breakpoint are uncertainty, which will result in an inability to resolve whether the embryo carries a balanced translocation.

In addition to the above technical defects, all the above detection techniques can not accurately determine the position of the balanced translocation breakpoint. If the position of the breakpoint is not determined accurately to a certain extent, a recombination interchange may occur, which will result in an inaccurate determination of whether an embryo carries the balanced translocation.

Although MicroSeq-PGD can accurately determine the position of the balanced translocation breakpoint, it involves processes including cell culture and micro-cutting, and has limitations such as complicated operation, long detection cycle, expensive, and high requirements for personnel and instruments, and thus cannot be applied on a large scale.

Therefore, there is an urgent need in the art to develop a method for more effectively and comprehensively identifying a balanced translocation in an embryo to improve the accuracy in determining a balanced translocation.

SUMMARY OF THE INVENTION

In view of the deficiencies in the prior art and actual demands, the present application provides methods for identifying a balanced translocation breakpoint and for determining a balanced translocation-carrying status in an embryo. The methods can not only accurately determine the position of the balanced translocation breakpoint, but also enable the accurate determination, haplotyping, and identification of embryos that do not carry a balanced translocation by using a small number of SNP loci.

To achieve this purpose, the present application uses the following technical solutions.

In the first aspect, the present application provides a method for identifying a balanced translocation breakpoint in an embryo, which comprises the following steps:

(1) obtaining a sample to be tested from an embryo and DNA from the parents;

(2) amplifying the sample to be tested, and constructing a library followed by sequencing;

(3) aligning genome sequencing reads obtained in step (2) to a reference genome to obtain position information of the genome sequencing reads aligned on the reference genome;

(4) dividing the reference genome into N region segments, each of which is taken as a window, and calculating the copy number of each window;

(5) determining the threshold range of the normal copy numbers, calculating the trimean $M_i$ of the copy numbers of each window and surrounding windows window-by-window, recording the windows with a $M_i$ that does not fall within the threshold range, and combining successive windows until a normal window is encountered;

(6) defining the successive windows as described in step (5) as a level 1 region, and further calculating the trimean $M_{nps}$ of each window in the level 1 region and surrounding windows, wherein the first window is recorded as the first breakpoint $bp_1$ and the normal and abnormal transition window is recorded as breakpoint $bp_i$;

(7) defining the region between two breakpoints as a level 2 region, and further calculating the trimean $M_j$ of each window in the level 2 region, wherein the window with a $M_j$ that falls outside the threshold range is the precise copy number variation region, and the start and end positions of the region are the start and end breakpoints of the copy number variation; and (8) selecting multiple embryos with an abnormal copy number, calculating the balanced translocation breakpoints on two chromosomes in each embryo by using steps (1)-(7), and calculating the trimean of the balanced translocation breakpoints on the two chromosomes respectively, which is the precise balanced translocation breakpoint in the embryo;

wherein i and j are independently any positive integer from 1 to N.

According to the present application, the sample to be tested as described in step (1) is a biopsy cell of the embryo. The biopsy cell is an ectodermal cell collected from the embryo when it develops to the blastomere or blastocyst stage. The ectodermal cell may be one or a plurality of trophectoderm cells.

According to the present application, the parent DNA may be extracted from any available human-origin specimen. It is not particularly limited herein, and can be obtained by extraction by those skilled in the art according to experimental demands. In the present application, the parent DNA may be extracted from any one of the group consisting of peripheral blood, lymph, tissue cells, hair and oral mucosal cells, or a combination of at least two thereof, and preferably from peripheral blood.

In the present application, the amplification as described in step (2) is a single cell amplification. A small amount of nucleic acids in the biopsy cell is amplified by the single cell amplification to obtain more nucleic acids for subsequent analysis.

In the present application, the single cell amplification is any method capable of performing a single cell amplification. It is not particularly limited herein and may be selected by those skilled in the art according to the experimental demands. The present application may adopt any one of the group consisting of Primer Extension Preamplification PCR (PEP-PCR), Degenerate Oligonucleotide Primer-PCR (DOP-PCR), Multiple Displacement Amplification (MDA) and Multiple Annealing and Looping Based Amplification Cycles (MALBAC), or a combination of at least two thereof, and preferably Multiple Annealing and Looping Based Amplification Cycles is used.

In the present application, the sequencing as described in step (2) is performed by using a high throughput sequencing platform after constructing a library with the amplified sample. The high throughput sequencing platform is a next generation sequencing platform. Any next generation sequencing platform in the field is feasible. It is not particularly limited herein, and may be selected by those skilled in the art according to demands. The present application may adopt any one of the group consisting of GA, GAII, GAIIx, HiSeq1000/2000/2500/3000/4000, X Ten, X Five, NextSeq500/550, MiSeq, MiSeqDx, MiSeq FGx, MiniSeq, and NovaSeq 5000/6000 available from Illumina, SOLiD available from Applied Biosystems, 454 FLX available from Roche, Ion Torrent, Ion PGM, and Ion Proton I/II available from Thermo Fisher Scientific (Life Technologies), BGISEQ1000, BGISEQ500, BGISEQ100, and BGISEQ50 available from BGI, BioelectronSeq 4000 available from CapitalBio, DA8600 available from Da An Gene Co., Ltd. of Sun Yat-Sen University, NextSeq CN500 available from Berry Genomics, BIGIS available from Zhongke Zixin (a subsidiary of Zixin Pharmaceutical), and HYK-PSTAR-IIA available from HYK Gene. The HiSeq 2500 high throughput sequencing platform available from Illumina is preferably used in the present application.

Preferably, the sequencing is single-end sequencing and/or paired-end sequencing, and preferably single-end sequencing.

According to the present application, the sequencing is performed at a sequencing read length of no less than 30 bp, such as 30 bp, 40 bp, 50 bp, 80 bp, 100 bp, 150 bp, 300 bp or 500 bp, and preferably 50 bp. Specific point values between the above values are also included, but are no longer listed exhaustively herein due to the limitation of space and for concise considerations.

According to the present application, the sequencing is performed at a sequencing depth of no less than 0.1 times, such as 0.1 times, 0.5 times, 1 time, 2 times, 5 times, 10 times, 30 times, 50 times, and 100 times, and preferably 0.1 times of the genome. Specific point values between the above values are also included, but are no longer listed exhaustively herein due to the limitation of space and for concise considerations.

Preferably, in the present application, the sequencing is performed by using a MALBAC single cell amplification method, HiSeq2500 high-throughput sequencing platform available from Illumina, and a single-end sequencing procedure, at a sequencing read length of 50 bp and a sequencing depth of 0.1 times of the genome.

In the present application, the reference genome may be a whole genome, or may be a part of the whole genome, for example, the reference genome covers 50% or more, such as 50%, 55%, 60%, 65%, 70%, 75%, 80%, 85%, 90%, 95%, 98%, preferably 60% or more, further preferably 70% or more, even preferably 80% or more, and most preferably 95% or more of the whole genome. Specific point values between the above values are also included, but are no longer listed exhaustively herein due to the limitation of space and for concise considerations.

When the reference genome is a whole genome, the whole genome typically is a sequence that has been generally identified, such as hg18 (GRCh18), hg19 (GRCh19), or hg38 (GRCh38) from NCBI or UCSC in terms of human genome.

According to the present application, the alignment of the genome sequencing reads to the reference genome may be performed by using any software, free or commercial available, in the art capable of aligning sequences. It is not particularly limited herein, and may be selected by those skilled in the art according to demands. For example, it may be any one of the group consisting of BWA (Burrows-Wheeler Alignment tool), SOAPaligner/soap2 (Short Oligonucleotide Analysis Package), and Bowtie/Bowtie2.

According to the present application, the window as described in step (4) has a length of $1\times10^2$-$1\times10^6$, such as $1\times10^2$, $2\times10^2$, $5\times10^2$, $8\times10^2$, $1\times10^3$, $5\times10^3$, $8\times10^3$, $1\times10^4$, $5\times10^4$, $1\times10^5$, $5\times10^5$, $8\times10^5$, or $1\times10^6$. Specific point values between the above values are also included, but are no longer listed exhaustively herein due to the limitation of space and for concise considerations.

According to the present application, the step (4) further comprises a step of correcting the copy number of each window and calculating the corrected copy number of each window. Any method in the art capable of correcting the copy number of a window may be used. It is not particularly limited herein, and those skilled in the art can select according to demands. In the present application, Loess correction is used.

According to the present application, the number and base distribution of the reads falling into each window, and the base distribution of the reference genome are calculated according to the positions of the sequenced reads aligned on the genome. The copy number of each window is corrected according to the reads and the base GC content in each window to obtain a corrected copy number of each window.

In the present application, the threshold range as described in step (5) is between N−σ and N+σ, wherein N is the ploidy of the sample to be tested, and σ is a predetermined value of a normal fluctuation range of the copy number, which is from 0.05 to 0.2, such as 0.05, 0.06, 0.08, 0.1, 0.12, 0.15, 0.18, or 0.2. Specific point values between the above values are also included, but are no longer listed exhaustively herein due to the limitation of space and for concise considerations.

In the case of a human being which is diploid, N=2, and the predetermined value (σ) of the normal fluctuation range is set to be 0.05, and as such the threshold range of the normal copy numbers is (2−0.05, 2+0.05).

Alternatively, the threshold range as described in step (5) is between N−m×SD and N+m×SD, wherein N is the ploidy of the sample to be tested, m is any integer from 1 to 3, and SD is the standard deviation of the copy numbers of all windows of the sample to be tested.

In the present application, when calculating the copy number, the genome is divided into several windows, and each window has a copy number. The copy numbers of most windows are normal and fluctuate around 2, and comply with the normal distribution. m is a multiple of the standard deviation. Theoretically, when m=1, 68.3% of values fall within [N−SD, N+SD]; when m=2, 95.5% of values fall within [N−2×SD, N+2×SD]; and when m=3, 99.7% of values fall within [N−3×SD, N+3×SD]. m is a statistical concept, and may be selected by those skilled in the art according to the actual situation.

In the case of a human being, the threshold range of the normal copy numbers may be (2−2×SD, 2+2×SD).

In the present application, both thresholds can be used for subsequent experiments. The σ in the threshold range "N−σ to N+σ" is generally obtained based on the distribution feature of the copy numbers of a large number of samples, and is suitable for most cases. The SD in the threshold range "N−m×SD to N+m×SD" is calculated based on the distribution feature of the copy numbers of the sample to be tested itself, and has a wider application scope and is suitable for all cases.

According to the present application, the number of the surrounding windows as described in step (5) is from 10 to 1000, such as 10, 12, 15, 20, 30, 40, 50, 60, 70, 80, 90, 100, preferably from 10 to 60, and further preferably 10. Specific point values between the above values are also included, but are no longer listed exhaustively herein due to the limitation of space and for concise considerations.

Preferably, the trimean is calculated according to the following formula: $M=Q1/4+M_d/2+Q3/4$, wherein Q1 is the lower quartile, $M_d$ is the median, and Q3 is the upper quartile.

Preferably, the number of the surrounding windows as described in step (6) is from 3 to 10, such as 3, 4, 5, 6, 7, 8, 9, 10, preferably from 3 to 8, and further preferably from 3 to 5. Specific point values between the above values are also included, but are no longer listed exhaustively herein due to the limitation of space and for concise considerations.

The normal and abnormal transition window as described in step (6) is determined as follows: defining the first window as the first breakpoint $bp_1$; calculating each window one-by-one, and recording the window as the second breakpoint $bp_2$ when at least two consecutive $M_{nps}$ fall within an abnormal range; go on scanning until at least two consecutive $M_{nps}$ return to the normal range, and recording the window as the third breakpoint $bp_3$. In this way, each time a normal and abnormal transition window is encountered, a breakpoint $bp_i$ is recorded until the last window of the level 1 region, wherein the i is any positive integer from 1 to M.

According to the present application, for the embryo copy number variation caused by the gametes carrying unbalanced translocation, the detected breakpoint is the balanced translocation breakpoint.

Preferably, the number of the multiple embryos as described in step (8) is a positive integer greater than 5.

In step (8), the balanced translocation breakpoint in the embryo is determined as follows: obtaining n embryos by IVF, in which there are n' embryos having an abnormal copy number, as detected by the above method, including unwanted embryos that are considered as unqualified during biopsy; selecting n" embryos having an abnormal copy number, wherein n" is a positive integer less than or equal to n', and preferably n"=n'; identifying the breakpoints on two cross-translocated chromosomes which are designated as chrM and chrN respectively, wherein for the n" embryos having an abnormal copy number, there would be nM" breakpoint positions on chrM and nN" breakpoint positions on chrN; and calculating the trimeans of the breakpoint positions on both chromosomes separately to obtain $bp_{chrM}$ and $bp_{chrN}$ which are the exact breakpoint positions on the two cross-translocated chromosomes.

In the second aspect, the present application provides a method for determining a balanced translocation-carrying status in an embryo, which comprises the following steps:

(1') identifying the balanced translocation breakpoint in the embryo by using the method as described in the first aspect;

(2') detecting SNPs around the breakpoint;

(3') embryo haplotype analysis: selecting effective SNPs, haplotyping one parent according to the SNP genotypes thereof, constructing the haplotype of the other parent by reference to the embryos having a normal copy number, and comparing with the haplotypes of the embryos having an abnormal copy number to determine the haplotyping results;

(4') determination of the carrying status of the embryo: haplotyping the embryos having a normal copy number, and then classifying the haplotypes into translocation-carrying and non-translocation-carrying ones to determine the haplotyping results; and (5') determination of the carrying status of the embryo: haplotyping the embryos having a normal copy number, and then comparing with the haplotyping results as described in step (4') to determine the translocation-carrying status of the embryo.

According to the present application, the length around the breakpoint in step (2') is $2\times10^5$-$5\times10^6$, such as $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, and preferably $2\times10^5$-$1\times10^6$. Specific point values between the above values are also included, but are no longer listed exhaustively herein due to the limitation of space and for concise considerations.

Preferably, the number of the SNPs as described in step (2') is generally 30 or more, and the available loci on each embryo account for about ⅓. The haplotype linkage relationship can be determined with 10 or more available loci. In the present application, the number of the SNPs is from 10 to 500, such as 10, 20, 30, 40, 50, 60, 80, 100, 120, 130, 150, 200, 250, 300, 350, 400, 450, 500, preferably from 30 to 100. Specific point values between the above values are also included, but are no longer listed exhaustively herein due to the limitation of space and for concise considerations.

According to the present application, methods for detecting SNPs around the breakpoint are well known in the art. They are not particularly limited herein, and may be selected by those skilled in the art according to demands. Any one method of the group consisting of designing probe array and performing target sequencing, designing primers and subjecting the amplicon to first generation sequencing, and designing primers and subjecting the amplicon to next generation sequencing, or a combination of at least two thereof may be used in the present application.

In the present application, in case of the first generation sequencing, the genotype is determined based on the peak map of the sequencing results; in case of the next generation sequencing, followed by the above steps (sequencing, aligning the genome sequences to the reference genome), analysis is performed by using a analysis software which may be any one of the group consisting of SAMtools, GATK, Varscan and the like, or a combination of at least thereof, to determine the genotype.

According to the present application, the effective SNPs are homozygous in one parent and heterozygous in the other parent, and the number of effective SNPs is from 10 to 500.

In the present application, said selecting effective SNPs is performed specifically as follows. The species to be detected is human which is diploid. One parent of the embryo is a translocation carrier, and the other is normal (non-carrier). As the translocation carrier contains cross-translocated M and N chromosomes as well as normal M and N chromosomes, he or she has normal chromosome chrM, translocation-derived chromosome der (chrM), normal chromosome chrN, and translocation-derived chromosome der (chrN). The normal parent has normal chromosomes chrM', chrM", chrN', and chrN". According to the Mendelian inheritance law and the Chain and Exchange law, SNPs that can effectively distinguish the haplotypes of normal chromosomes and translocation-derived chromosomes are selected upstream and downstream of the breakpoint.

In the present application, the carrying status in the embryo is specifically determined as follows: examining each embryo having a normal copy number according to the haplotyping results of two chromosomes; identifying the chromosome that is inherited from the translocation carrier (among the parents), so as to identify the translocation-carrying embryo, wherein if the chromosome is the same as the translocated chromosome, the embryo carries the translocation, and if the chromosome is the same as the normal chromosome, the embryo doesn't carry the translocation (normal).

According to the present application, the method for determining a balanced translocation-carrying status in an embryo comprises the following steps:

(1) obtaining a sample to be tested from an embryo and DNA from the parents;
(2) amplifying the sample to be tested, and constructing a library followed by sequencing;
(3) aligning the genome sequencing reads obtained in step (2) to a reference genome to obtain position information of the genome sequencing reads aligned on the reference genome;
(4) dividing the reference genome into N region segments, each of which is taken as a window, and calculating the copy number of each window;
(5) determining the threshold range of the normal copy numbers, calculating the trimean Mi of the copy numbers of each window and surrounding windows window-by-window, recording the windows with a Mi that does not fall within the threshold range, and combining successive windows until a normal window is encountered;
(6) defining the successive windows as described in step (5) as a level 1 region, and further calculating the trimean $M_{nps}$ of each window in the level 1 region and surrounding windows, wherein the first window is recorded as the first breakpoint bp1 and the normal and abnormal transition window is recorded as breakpoint bpi;
(7) defining the region between two breakpoints as a level 2 region, and further calculating the trimean $M_j$ of each window in the level 2 region, wherein the window with a $M_j$ that falls outside the threshold range is the precise copy number variation region, and the start and end positions of the region are the start and end breakpoints of the copy number variation;
(8) selecting multiple embryos with an abnormal copy number, calculating the balanced translocation breakpoints on two chromosomes in each embryo by using steps (1)-(7), and calculating the trimean of the balanced translocation breakpoints on the both chromosomes, respectively, which is the precise balanced translocation breakpoints in the embryo;
(9) detecting SNPs around the breakpoint;
(10') embryo haplotype analysis: selecting effective SNPs, haplotyping one parent according to the SNP genotypes thereof, constructing the haplotype of the other parent by reference to the embryos having a normal copy number, and comparing with the haplotypes of the embryos having an abnormal copy number to determine the haplotyping results; and
(11) determination of the carrying status of the embryo: haplotyping the embryos having a normal copy number, and then comparing with the haplotyping results as described in step (10) to determine the translocation-carrying status in the embryo;

wherein i and j are independently any positive integer from 1 to N.

Compared with the prior art, the present application has the following beneficial effects:

(1) The present application provides a method for accurately determining the position of a balanced translocation breakpoint, so that the resolution in determining a breakpoint is greatly improved, SNPs can be detected in a more accurate and effective region, and the occurrence of recombination exchange is avoided.
(2) By means of the deduction between embryos, the present application uses a small number of embryos and SNPs to enable the accurate haplotyping and the determination of a balanced translocation-carrying status in an embryo, which greatly saves cost and improves accuracy;
(3) The detection method of the present application is applicable to a wider population, involves more simple operation flow, and takes shorter detection time period.

DESCRIPTION OF THE DRAWINGS

FIG. 1 is a flow chart of the method for determining a balanced translocation-carrying status in an embryo according to the present application.

DETAILED DESCRIPTION

The technical solutions of the present application and effects thereof are further described below with reference to the accompanying drawing and specific examples, but the present application is not limited to the scope of the examples.

The present application has been applied to 30 cases. After clinical verification, the coincidence rate between the test results and the actual clinical results was 100%. In order to facilitate understanding and mastering of the usage and effects of the present application, an example will be further described below. The brief flow chart of the example is shown in FIG. 1. The detailed implementation process is as follows.

In this example, samples from embryos of a balanced translocation carrier and the family thereof were tested, and the identification results were compared with the gold standard used in clinical karyotype detection, that is, amniotic water puncture verification.

In this family, the father had a normal karyotype, and the mother was a carrier of balanced translocation between chr7 and chr16, with a karyotype of 46,XX,t(7; 16)(p12.3; q22.1).

The specific implementation process was as follows.

Example 1 Identification of Balanced Translocation Breakpoints (1) Obtaining Embryo Samples to be Tested and the Parents' DNA 8 embryos were obtained (represented by E1, E2, E3, E4, E5, E6, E7 and E8, respectively) from this family by IVF, and 3-5 trophectoderm cells were collected from each embryo biopsy when the embryo developed to the blastocyst stage.

(2) Amplification and Sequencing of the Samples

Single cell amplification was performed by using the Multiple Annealing and Looping-based Amplification Cycles Single Cell Whole Genome Amplification Kit YK001A available from Yikon Genomics (Shanghai) Co., Ltd according to the manufacturer's instructions to amplify the whole genome of the embryo biopsy cell.

Sequencing was performed by using the HiSeq2500 high-throughput sequencing platform available from Illumina according to the manufacturer's instructions. The sequencing was performed in a single-end manner, and at a read length of 50 bp and a sequencing depth of 0.1 times of the genome.

(3) Sequence Alignment and Copy Number Analysis

Adaptors and low-quality data were removed from the sequencing results which were then aligned to the hg19 reference genome (GRCh19) by using the software BWA (Burrows-Wheeler Alignment tool) with default parameters to obtain positions of the reads aligned on the genome. The reads that were uniquely aligned on the genome were selected.

The genome was divided into windows with a length of $5 \times 10^7$ bp. The number and base distribution of the reads falling into each window and the base distribution of the reference genome were calculated based on the positions of the reads aligned on the genome. The copy number in each window was corrected by Loess according to the reads and the base GC content in each window.

The copy number results were shown in Table 1. Only the copy numbers in partial regions of chr7 were shown in Table 1 as the human genome was very large ($3 \times 10^9$ bp).

TABLE 1

Copy numbers in partial regions of chr7 of each embryo

| Chromosome | Region | E1 | E2 | E3 | E4 | E5 | E6 | E7 | E8 |
|---|---|---|---|---|---|---|---|---|---|
| chr7 | 44650001-44700000 | 1.71 | 2.08 | 0.86 | 2.11 | 2.14 | 2.19 | 3.22 | 3.08 |
| chr7 | 44700001-44750000 | 1.93 | 2.40 | 0.96 | 2.17 | 2.02 | 2.22 | 2.92 | 3.20 |
| chr7 | 44750001-44800000 | 2.25 | 2.09 | 1.07 | 2.24 | 1.93 | 2.02 | 2.79 | 3.22 |
| chr7 | 44800001-44850000 | 2.16 | 2.01 | 1.12 | 2.41 | 2.08 | 1.98 | 2.49 | 3.38 |
| chr7 | 44850001-44900000 | 2.27 | 2.09 | 1.24 | 2.31 | 2.01 | 2.00 | 3.03 | 3.55 |
| chr7 | 44900001-44950000 | 1.94 | 2.16 | 0.97 | 2.03 | 1.83 | 1.90 | 2.71 | 2.94 |
| chr7 | 44950001-45000000 | 2.13 | 2.14 | 0.83 | 1.89 | 1.83 | 2.11 | 2.32 | 2.45 |
| chr7 | 45000001-45050000 | 1.83 | 1.97 | 0.89 | 2.00 | 2.02 | 2.25 | 2.28 | 2.22 |
| chr7 | 45050001-45100000 | 1.97 | 1.97 | 1.08 | 2.18 | 2.30 | 2.30 | 2.53 | 2.70 |
| chr7 | 45100001-45150000 | 1.84 | 2.04 | 1.09 | 2.29 | 2.36 | 2.18 | 2.73 | 2.88 |
| chr7 | 45150001-45200000 | 1.78 | 2.01 | 1.06 | 2.21 | 2.27 | 2.11 | 2.88 | 2.93 |
| chr7 | 45200001-45250000 | 1.79 | 1.95 | 0.96 | 2.28 | 2.32 | 1.88 | 3.14 | 2.98 |
| chr7 | 45250001-45300000 | 1.68 | 2.02 | 1.18 | 1.96 | 2.18 | 2.00 | 3.10 | 2.87 |
| chr7 | 45300001-45350000 | 1.77 | 2.11 | 1.07 | 2.19 | 2.02 | 1.92 | 3.13 | 2.95 |
| chr7 | 45350001-45400000 | 2.03 | 1.96 | 1.03 | 2.07 | 1.77 | 2.28 | 3.03 | 2.78 |
| chr7 | 45400001-45450000 | 2.10 | 1.86 | 0.92 | 2.05 | 2.03 | 2.14 | 2.97 | 2.69 |
| chr7 | 45450001-45500000 | 2.10 | 1.93 | 0.87 | 2.01 | 1.98 | 2.35 | 2.77 | 2.85 |
| chr7 | 45500001-45550000 | 2.14 | 1.90 | 1.05 | 1.96 | 2.20 | 2.04 | 2.91 | 2.92 |
| chr7 | 45550001-45600000 | 2.10 | 1.96 | 1.09 | 2.09 | 2.16 | 2.06 | 2.95 | 3.12 |
| chr7 | 45600001-45650000 | 2.09 | 2.01 | 1.08 | 2.19 | 2.26 | 2.02 | 3.12 | 3.09 |
| chr7 | 45650001-45700000 | 2.15 | 2.07 | 1.05 | 2.20 | 2.15 | 2.27 | 3.09 | 3.29 |
| chr7 | 45700001-45750000 | 1.93 | 2.05 | 0.95 | 2.19 | 2.15 | 2.30 | 2.76 | 3.04 |
| chr7 | 45750001-45800000 | 2.10 | 2.12 | 0.98 | 2.07 | 2.49 | 2.18 | 2.69 | 2.74 |
| chr7 | 45800001-45850000 | 2.28 | 1.85 | 1.39 | 2.13 | 2.21 | 2.18 | 2.27 | 2.30 |
| chr7 | 45850001-45900000 | 2.60 | 1.94 | 1.71 | 2.03 | 2.17 | 1.85 | 1.99 | 1.81 |
| chr7 | 45900001-45950000 | 2.49 | 2.05 | 2.06 | 2.09 | 2.14 | 1.93 | 1.79 | 1.75 |
| chr7 | 45950001-46000000 | 2.55 | 2.19 | 1.68 | 2.11 | 2.29 | 1.81 | 1.88 | 1.77 |
| chr7 | 46000001-46050000 | 2.75 | 2.04 | 1.73 | 2.03 | 2.48 | 2.08 | 1.93 | 1.86 |
| chr7 | 46050001-46100000 | 2.94 | 1.66 | 1.78 | 1.97 | 2.57 | 2.00 | 1.96 | 1.66 |
| chr7 | 46100001-46150000 | 3.17 | 2.08 | 2.00 | 2.17 | 2.48 | 2.04 | 2.11 | 1.68 |
| chr7 | 46150001-46200000 | 3.08 | 1.87 | 1.87 | 2.05 | 2.35 | 1.95 | 1.89 | 1.80 |
| chr7 | 46200001-46250000 | 3.35 | 2.00 | 1.75 | 2.15 | 2.35 | 1.84 | 2.14 | 2.11 |
| chr7 | 46250001-46300000 | 3.08 | 2.14 | 1.73 | 2.12 | 2.27 | 1.99 | 2.04 | 1.77 |
| chr7 | 46300001-46350000 | 3.14 | 2.32 | 1.79 | 2.08 | 2.09 | 1.94 | 2.06 | 1.77 |
| chr7 | 46350001-46400000 | 2.98 | 2.26 | 2.17 | 2.05 | 1.98 | 1.99 | 2.07 | 1.85 |
| chr7 | 46400001-46450000 | 3.19 | 2.53 | 2.31 | 2.01 | 2.06 | 1.74 | 1.89 | 1.78 |
| chr7 | 46450001-46500000 | 2.99 | 2.28 | 2.33 | 2.25 | 2.13 | 1.78 | 1.90 | 1.86 |
| chr7 | 46500001-46550000 | 3.18 | 2.22 | 2.24 | 2.23 | 1.98 | 1.80 | 1.87 | 1.96 |
| chr7 | 46550001-46600000 | 3.00 | 2.10 | 2.12 | 2.38 | 2.01 | 1.99 | 1.90 | 2.04 |
| chr7 | 46600001-46650000 | 2.95 | 1.87 | 1.96 | 2.20 | 1.94 | 1.93 | 1.65 | 2.07 |
| chr7 | 46650001-46700000 | 3.00 | 2.05 | 1.90 | 2.18 | 1.94 | 2.00 | 1.82 | 2.09 |
| chr7 | 46700001-46750000 | 2.78 | 2.02 | 1.90 | 2.03 | 1.82 | 2.06 | 1.93 | 2.09 |
| chr7 | 46750001-46800000 | 2.52 | 2.39 | 2.01 | 2.31 | 1.75 | 2.03 | 1.85 | 2.00 |
| chr7 | 46800001-46850000 | 2.81 | 2.24 | 2.23 | 2.41 | 2.13 | 1.94 | 1.86 | 1.82 |

TABLE 1-continued

Copy numbers in partial regions of chr7 of each embryo

| Chromosome | Region | E1 | E2 | E3 | E4 | E5 | E6 | E7 | E8 |
|---|---|---|---|---|---|---|---|---|---|
| chr7 | 46850001-46900000 | 3.14 | 2.18 | 2.38 | 2.29 | 2.07 | 1.85 | 1.79 | 1.89 |
| chr7 | 46900001-46950000 | 3.20 | 2.27 | 2.24 | 2.23 | 2.06 | 1.77 | 1.98 | 1.68 |
| chr7 | 46950001-47000000 | 3.13 | 2.32 | 2.09 | 2.45 | 2.01 | 2.00 | 1.82 | 1.85 |
| chr7 | 47000001-47050000 | 3.02 | 2.35 | 2.25 | 2.11 | 2.11 | 2.13 | 1.99 | 1.82 |
| chr7 | 47050001-47100000 | 3.00 | 2.24 | 2.18 | 2.20 | 2.12 | 2.09 | 1.69 | 1.92 |
| chr7 | 47100001-47150000 | 3.05 | 2.30 | 2.30 | 2.19 | 2.09 | 2.00 | 1.64 | 2.05 |
| chr7 | 47150001-47200000 | 2.93 | 2.24 | 2.05 | 2.14 | 2.08 | 2.37 | 1.58 | 1.94 |
| ... | ... | ... | ... | ... | ... | ... | ... | ... | ... |

(4) Accurate Determination of the Position of the Breakpoint

Through the above steps, the copy number of each window was obtained. The range of the normal copy numbers was set up by the following method: the standard deviation (SD) of the copy numbers of all windows of the sample was calculated according to the distribution feature of the copy numbers of the sample, and the threshold range of the normal copy numbers was determined as the normal value ±2 times the standard deviation. In this example, SD=0.11 and thus the range was (1.78, 2.22).

The trimean $M_i$ of the copy numbers of each window and 10 surrounding windows was calculated window-by-window. The windows with a trimean $M_i$ that fell outside the threshold range were recorded, and successive windows were combined until a normal window was encountered.

Through the above calculation, successive windows having an abnormal copy number were obtained and defined as a level 1 region. The first window in the level 1 region was defined as the first breakpoint $bp_1$, and then the trimean $M_{nps}$ of each window in the level 1 region and 3 surrounding windows was calculated window-by-window. When at least two consecutive $M_{nps}$ fell within the abnormal range, the window was recorded as the second breakpoint $bp_2$. The scan was continued until at least two consecutive $M_{nps}$ returned to the normal range, and the window was recorded as the third breakpoint $bp_3$. In this way, each time a normal and abnormal transition window was encountered, a breakpoint $bp_i$ was recorded until the last window of the level 1 region which was recorded as $bp_f$.

The level 1 region was divided by breakpoints from $bp_1$ to $bp_f$ into (f–1) secondary segments which were defined as level 2 regions. The trimean $M_j$ of the copy number of each window in the level 2 region was calculated, and compared with the normal range of the copy number. The level 2 region with a $M_j$ that fell within the abnormal range was the precise copy number variation region, wherein $M_j$ was the copy number in this region, and the start and end positions of this region were the start and end breakpoints of the copy number variation. For embryo copy number variation caused by unbalanced gametes, the detected breakpoints were the balanced translocation breakpoints.

In this example, 8 embryos were obtained, in which 4 embryos had an abnormal copy number, as detected by the above method, and were designated as E1, E3, E7, and E8, respectively. The breakpoints on two cross-translocated chromosomes were determined for all of the 4 embryos having an abnormal copy number. For all of the 4 embryos having an abnormal copy number, 4 breakpoint positions were obtained on chr7 and 4 breakpoint positions were also obtained on chr16. The trimeans of the breakpoint positions on the two chromosomes were calculated separately, and the precise breakpoint positions of the two cross-translocated chromosomes were obtained, and were designated as chr7: 45,900,001±50,000 and chr16: 43,100,001±50,000. The detection results were shown in Table 2.

TABLE 2

Determination of the precise breakpoints according to the breakpoints in 4 embryos having an abnormal copy number

| | Chromosome | |
|---|---|---|
| Embryo | chr7 | chr16 |
| E1 | 45,950,001-46,000,000 | 43,000,001-43,050,000 |
| E3 | 45,850,001-45,900,000 | 43,150,001-43,200,000 |
| E7 | 45,950,001-46,000,000 | 43,050,001-43,100,000 |
| E8 | 45,900,001-45,950,000 | 43,150,001-43,200,000 |
| Precise breakpoint | 45,900,001 ± 50,000 | 43,100,001 ± 50,000 |

Example 2 Determination of the Balanced Translocation-Carrying Status in an Embryo (1') Precise Balanced Translocation Breakpoints in the Embryos were Obtained from Example 1

(2') SNPs Around the Breakpoints were Detected

The embryos and their parents were detected for 61 SNP loci within 1×10$^6$ bp away from the chr7 breakpoint and 63 SNP loci within 1×10$^6$ bp away from the chr16 breakpoint by designing primers and subjecting the amplicon to next generation sequencing. The SNP genotypes were determined by using the next generation sequencing and using the analysis software SAMtools.

The genotyping results for SNPs upstream and downstream of chr7 and chr16 breakpoints of this family were shown in Tables 3 and 4.

TABLE 3

Genotypes of SNPs upstream and downstream of the chr7 breakpoint of the family sample

| SNP No. | Father | Mother | E1 | E2 | E3 | E4 | E5 | E6 | E7 | E8 |
|---|---|---|---|---|---|---|---|---|---|---|
| 1 | C/C | T/T | T/C | T/C | C/C | T/C | T/C | T/C | T/C | T/C |
| 2 | A/A | C/C | A/C | A/C | A/A | A/C | A/C | A/C | A/C | A/C |

TABLE 3-continued

Genotypes of SNPs upstream and downstream of the chr7 breakpoint of the family sample

| SNP No. | Father | Mother | E1 | E2 | E3 | E4 | E5 | E6 | E7 | E8 |
|---|---|---|---|---|---|---|---|---|---|---|
| 3 | G/G | T/T | T/G | T/G | — | — | T/G | T/G | G/G | T/G |
| 4 | C/C | T/T | T/C | T/C | C/C | T/C | T/C | T/C | T/C | T/C |
| 5 | G/G | A/A | A/G | A/G | G/G | A/G | A/G | A/G | A/G | A/G |
| 6 | T/T | G/G | G/T | G/T | T/T | T/T | G/T | G/T | G/T | G/T |
| 7 | A/A | G/A | G/A | G/A | A/A | G/A | G/A | A/A | G/A | G/A |
| 8 | G/G | G/G | G/G | G/G | G/G | — | G/G | G/G | G/G | G/G |
| 9 | G/A | G/G | G/A | G/A | A/A | G/G | G/A | G/A | G/G | G/A |
| 10 | A/A | C/A | C/A | A/A | A/A | A/A | A/A | C/A | A/A | C/A |
| 11 | T/G | T/G | T/G | G/G | T/T | — | T/G | T/G | G/G | T/G |
| 12 | G/T | G/G | G/T | G/G | T/T | G/G | G/T | G/G | G/G | G/T |
| 13 | G/G | G/G | G/G | G/G | G/G | G/G | G/G | G/G | G/G | G/G |
| 14 | C/T | T/T | C/T | T/T | C/C | T/T | C/T | T/T | T/T | C/T |
| 15 | G/G | G/G | G/G | G/G | G/G | G/G | G/G | G/G | G/G | G/G |
| 16 | A/A | G/A | G/A | G/A | A/A | G/A | G/A | A/A | G/A | G/A |
| 17 | A/G | A/G | A/G | A/G | A/A | A/G | A/A | G/G | A/G | A/G |
| 18 | T/C | T/T | T/C | T/T | C/C | — | T/C | T/T | T/T | T/C |
| 19 | G/T | G/G | G/T | G/G | T/T | G/G | G/T | G/G | G/G | G/T |
| 20 | G/T | G/G | G/T | G/G | T/T | G/G | G/T | G/G | G/G | G/T |
| 21 | T/G | T/T | T/G | T/T | G/G | T/T | T/G | T/T | T/T | T/G |
| 22 | G/A | A/A | G/A | A/A | G/G | A/A | G/A | A/A | A/A | G/A |
| 23 | T/T | C/T | C/T | T/T | T/T | T/T | T/T | C/T | T/T | C/T |
| 24 | T/T | C/T | C/T | C/T | T/T | C/T | C/T | T/T | C/T | C/T |
| 25 | C/T | C/T | C/T | C/T | T/T | G/A | T/T | C/C | C/T | C/T |
| 26 | T/C | T/C | T/C | T/C | C/C | — | C/C | — | T/C | T/C |
| 27 | G/C | G/C | G/C | — | — | — | C/C | G/G | G/C | G/C |
| 28 | C/C | T/C | T/C | C/C | C/C | C/C | C/C | T/C | C/C | T/C |
| 29 | T/C | T/C | T/C | T/C | — | T/C | C/C | T/T | T/C | T/C |
| 30 | G/A | A/A | A/A | G/G | A/A | G/A | A/A | G/A | G/A | A/A |
| 31 | G/C | G/G | G/C | G/G | G/C | G/G | G/C | G/G | G/G | G/C |
| 32 | T/C | T/C | T/C | C/C | T/T | C/C | T/C | T/C | T/C | T/C |
| 33 | A/G | A/G | A/G | G/G | A/A | G/G | A/G | A/G | A/G | A/G |
| 34 | C/T | C/T | C/T | C/C | T/T | — | C/T | C/T | C/T | C/T |
| 35 | G/A | A/A | A/A | G/A | A/A | G/G | A/A | G/A | G/A | A/A |
| 36 | G/A | A/A | A/A | G/A | A/A | G/A | A/A | G/A | G/A | A/A |
| 37 | T/T | T/A | T/A | T/A | T/T | — | T/A | T/T | T/T | T/A |
| 38 | C/C | T/T | T/C | T/C | T/C | T/T | T/C | T/C | T/C | T/C |
| 39 | A/A | G/G | A/G | A/G | A/G | A/G | A/G | A/G | A/G | A/G |
| 40 | G/C | G/C | G/G | C/C | C/C | G/G | G/G | C/C | G/C | G/G |
| 41 | G/G | G/G | G/G | G/G | G/G | G/G | G/G | G/G | G/G | G/G |
| 42 | G/A | G/A | G/G | G/A | G/A | A/A | G/G | A/A | G/A | G/G |
| 43 | A/A | G/A | G/A | G/A | A/A | G/A | A/A | G/A | G/A | G/A |
| 44 | T/C | T/T | T/T | T/C | T/T | T/C | T/T | T/C | T/C | T/T |
| 45 | T/G | T/T | T/T | T/G | T/T | — | T/T | T/G | T/G | T/T |
| 46 | A/G | G/G | — | — | G/G | — | G/G | A/A | A/G | G/G |
| 47 | T/T | T/T | T/T | T/T | T/T | T/T | T/T | T/T | T/T | T/T |
| 48 | C/C | C/C | C/C | C/C | C/C | C/C | C/C | C/C | C/C | C/C |
| 49 | G/G | G/G | G/G | G/G | G/G | — | G/G | G/G | G/G | G/G |
| 50 | A/G | A/G | A/A | A/G | A/G | — | A/A | G/G | A/G | A/A |
| 51 | A/A | A/G | A/A | A/A | A/G | A/A | A/A | A/G | A/G | A/A |
| 52 | G/G | A/A | G/A | G/A | G/G | — | G/A | G/A | G/A | G/A |
| 53 | G/G | G/G | G/G | G/G | G/G | G/G | G/G | G/G | G/G | G/G |
| 54 | A/A | A/G | A/G | A/G | A/A | A/G | A/G | A/A | A/G | A/G |
| 55 | G/A | G/G | G/A | G/G | G/A | — | G/A | G/G | G/G | G/A |
| 56 | C/C | C/T | T/T | C/T | C/C | — | C/T | C/C | C/T | C/T |
| 57 | C/A | G/G | G/A | G/G | G/A | G/G | G/A | G/G | G/G | G/A |
| 58 | G/T | G/G | G/T | G/G | G/T | G/G | G/T | G/G | G/G | G/T |
| 59 | G/A | A/A | G/A | A/A | G/A | — | G/A | A/A | A/A | G/A |
| 60 | G/A | G/A | A/A | G/A | G/A | — | A/A | G/G | G/A | A/A |
| 61 | C/T | C/T | C/T | C/C | T/T | C/C | C/T | C/T | C/T | C/T |

"—" indicates that the locus was undetectable, and the subsequent tables have the same indication method.

TABLE 4

Genotypes of SNPs upstream and downstream of the chr16 breakpoint of the family sample

| SNP No. | Father | Mother | E1 | E2 | E3 | E4 | E5 | E6 | E7 | E8 |
|---|---|---|---|---|---|---|---|---|---|---|
| 1 | C/C | C/T | C/C | C/T | C/T | C/T | C/T | C/C | C/C | C/C |
| 2 | T/T | T/C | T/C | T/T | T/T | T/T | T/T | T/C | T/T | T/C |
| 3 | T/T | C/T | — | — | T/T | — | T/T | C/T | — | C/T |
| 4 | A/A | C/C | — | C/C | — | C/A | C/A | C/A | — | C/A |

TABLE 4-continued

Genotypes of SNPs upstream and downstream of the chr16 breakpoint of the family sample

| SNP No. | Father | Mother | E1 | E2 | E3 | E4 | E5 | E6 | E7 | E8 |
|---|---|---|---|---|---|---|---|---|---|---|
| 5 | A/C | C/C | A/C | A/C | A/C | C/C | C/C | C/C | A/A | C/C |
| 6 | A/A | G/G | A/G | A/G | A/G | A/G | A/G | A/G | A/A | A/G |
| 7 | G/G | A/G | A/G | G/G | G/G | G/G | G/G | A/G | G/G | A/G |
| 8 | A/A | C/A | C/A | A/A | A/A | A/A | A/A | C/A | A/A | C/A |
| 9 | T/T | A/A | T/A | T/A | T/A | T/A | T/A | T/A | T/T | T/A |
| 10 | G/G | G/G | G/G | G/G | G/G | — | G/G | G/G | G/G | G/C |
| 11 | C/A | C/A | C/C | C/A | C/A | A/A | A/A | C/A | C/C | C/A |
| 12 | T/G | T/G | T/G | T/T | T/T | T/G | T/G | G/G | T/T | G/G |
| 13 | A/A | G/G | G/A | G/A | G/A | — | G/A | G/A | A/A | G/A |
| 14 | G/T | T/T | G/T | G/T | G/T | T/T | T/T | T/T | G/G | T/T |
| 15 | C/C | C/T | C/T | C/C | C/C | C/C | C/C | C/T | — | C/T |
| 16 | A/G | A/G | A/G | G/G | G/G | G/G | A/G | A/A | G/G | A/A |
| 17 | T/C | T/C | T/C | C/C | C/C | T/C | T/C | T/T | C/C | T/T |
| 18 | C/C | C/C | C/C | C/C | C/C | C/C | C/C | C/C | C/C | C/C |
| 19 | T/T | C/T | T/T | C/T | C/T | C/T | C/T | T/T | T/T | T/T |
| 20 | C/T | T/T | C/T | C/T | C/T | — | T/T | T/T | C/T | T/T |
| 21 | T/T | T/A | T/T | T/A | T/A | — | T/A | T/T | T/T | T/T |
| 22 | T/T | C/T | T/T | C/T | C/T | C/T | C/T | T/T | — | T/T |
| 23 | C/C | T/C | C/C | T/C | T/C | T/C | T/C | C/C | C/C | C/C |
| 24 | A/A | C/A | A/A | C/A | C/A | — | C/A | A/A | A/A | A/A |
| 25 | C/A | A/A | C/A | C/A | C/A | A/A | A/A | A/A | C/C | A/A |
| 26 | C/T | T/T | C/T | C/T | C/T | T/T | T/T | T/T | C/C | T/T |
| 27 | T/G | G/G | T/G | T/G | T/G | G/G | G/G | G/G | T/T | G/G |
| 28 | A/G | G/G | A/G | A/G | A/G | G/G | G/G | G/G | A/A | G/G |
| 29 | C/A | C/C | C/C | C/C | C/C | C/A | C/A | C/A | C/C | C/A |
| 30 | G/T | G/G | G/G | G/G | G/G | — | G/T | G/T | G/G | G/T |
| 31 | G/A | A/A | A/A | A/A | A/A | — | G/A | G/A | A/A | G/A |
| 32 | T/A | T/T | T/T | T/T | T/T | T/A | T/A | T/A | T/T | T/A |
| 33 | A/G | A/G | G/G | G/G | A/G | — | A/G | — | — | A/A |
| 34 | C/C | C/A | C/C | C/A | C/A | C/A | C/A | C/C | C/C | C/C |
| 35 | C/T | T/T | T/T | T/T | T/T | C/C | C/T | C/T | T/T | C/C |
| 36 | C/C | C/T | C/C | C/T | C/C | T/T | C/T | C/C | C/C | C/C |
| 37 | C/G | C/C | G/G | C/G | C/G | C/C | C/C | C/C | C/G | C/C |
| 38 | G/A | G/G | A/A | G/A | G/A | G/G | G/G | G/G | G/A | G/G |
| 39 | C/T | C/C | T/T | C/T | C/T | C/C | C/C | C/C | C/T | C/C |
| 40 | G/G | G/G | G/G | G/G | G/G | G/G | G/G | G/G | G/G | G/G |
| 41 | C/C | C/C | C/C | C/C | C/C | — | C/C | C/C | C/C | C/C |
| 42 | A/A | G/G | A/A | A/G | G/G | G/G | G/G | G/G | A/G | — |
| 43 | A/A | G/G | A/A | G/A | G/A | G/A | G/A | G/A | G/A | A/A |
| 44 | C/C | C/C | C/C | C/C | C/C | — | C/C | C/C | C/C | C/C |
| 45 | T/G | G/G | G/G | G/G | G/G | T/G | T/G | T/G | G/G | T/T |
| 46 | T/C | C/C | — | T/T | C/C | — | C/C | — | T/C | C/C |
| 47 | C/T | T/T | C/C | C/T | C/T | T/T | T/T | T/T | C/T | T/T |
| 48 | A/A | A/A | A/A | A/A | A/A | A/A | A/A | A/A | A/A | A/A |
| 49 | T/T | T/T | T/T | T/T | T/T | T/T | T/T | T/T | T/T | T/T |
| 50 | A/A | A/A | A/A | A/A | A/A | — | A/A | A/A | A/A | A/A |
| 51 | A/A | A/A | A/A | A/A | A/A | A/A | A/A | A/A | A/A | A/A |
| 52 | T/T | T/T | T/T | T/T | T/T | T/T | T/T | T/T | T/T | T/T |
| 53 | A/G | A/G | G/G | G/G | A/G | A/G | A/G | A/A | A/G | A/A |
| 54 | G/G | G/C | G/G | G/G | G/C | G/G | G/G | G/C | G/C | G/G |
| 55 | A/G | A/G | — | A/G | A/G | A/A | A/A | — | G/G | A/A |
| 56 | G/C | G/G | C/C | G/C | G/C | G/G | G/G | G/G | G/C | G/G |
| 57 | C/C | T/T | C/C | C/T | C/T | C/T | C/T | C/T | C/T | C/C |
| 58 | A/G | A/A | A/A | A/A | A/A | A/G | A/G | — | A/A | G/G |
| 59 | G/A | G/A | — | G/G | G/A | G/A | G/A | A/A | G/A | A/A |
| 60 | T/T | T/T | T/T | T/T | T/T | T/T | T/T | T/T | T/T | T/T |
| 61 | T/T | T/C | T/T | T/C | T/C | T/C | T/C | T/T | T/T | T/T |
| 62 | T/G | T/T | G/G | T/G | T/G | T/T | T/T | T/T | T/G | T/T |
| 63 | C/C | C/T | C/C | C/T | C/T | C/T | C/T | C/C | C/C | C/C |

(3') Embryo Haplotype Analysis

According to the Mendelian inheritance law and the Chain and Exchange law, effective informative SNPs were selected from the SNPs listed in Table 3-4, and were shown in Table 5.

TABLE 5

Genotypes of effective SNPs upstream and downstream of the breakpoints in the family sample

| Chromosome | SNP No. | Father | Mother | E1 | E2 | E3 | E4 | E5 | E6 | E7 | E8 |
|---|---|---|---|---|---|---|---|---|---|---|---|
| chr7 | 7 | A/A | G/A | G/A | G/A | A/A | G/A | G/A | A/A | G/A | G/A |
| chr7 | 10 | A/A | C/A | C/A | A/A | A/A | A/A | A/A | C/A | A/A | C/A |
| chr7 | 16 | A/A | G/A | G/A | G/A | A/A | G/A | G/A | A/A | G/A | G/A |
| chr7 | 23 | T/T | C/T | C/T | T/T | T/T | T/T | T/T | C/T | T/T | C/T |
| chr7 | 24 | T/T | C/T | C/T | C/T | T/T | C/T | C/T | T/T | C/T | C/T |
| chr7 | 28 | C/C | T/C | T/C | C/C | C/C | C/C | C/C | T/C | C/C | T/C |
| chr7 | 37 | T/T | T/A | T/A | T/A | T/T | — | T/A | T/T | T/T | T/A |
| chr7 | 43 | A/A | G/A | G/A | G/A | A/A | A/G | G/A | G/A | G/A | G/A |
| chr7 | 51 | A/A | A/G | A/A | A/A | A/G | A/A | A/A | A/G | A/G | A/A |
| chr7 | 54 | A/A | A/G | A/G | A/G | A/A | A/G | A/G | A/A | A/G | A/G |
| chr7 | 56 | C/C | C/T | T/T | C/T | C/C | — | C/T | C/C | C/T | C/T |
| chr16 | 1 | C/C | C/T | C/C | C/T | C/T | C/T | C/T | C/C | C/C | C/C |
| chr16 | 2 | T/T | T/C | T/C | T/T | T/T | T/T | T/T | T/C | T/C | T/C |
| chr16 | 3 | T/T | C/T | — | — | T/T | — | T/T | C/T | — | C/T |
| chr16 | 7 | G/G | A/G | A/G | G/G | G/G | G/G | G/G | A/G | G/C | A/G |
| chr16 | 8 | A/A | C/A | C/A | A/A | A/A | A/A | A/A | C/A | A/A | C/A |
| chr16 | 15 | C/C | C/T | C/T | C/C | C/C | C/C | C/C | C/T | — | C/T |
| chr16 | 19 | T/T | C/T | T/T | C/T | C/T | C/T | C/T | T/T | T/T | T/T |
| chr16 | 21 | T/T | T/A | T/T | T/A | T/A | — | T/A | T/T | T/T | T/T |
| chr16 | 22 | T/T | C/T | T/T | C/T | C/T | C/T | C/T | T/T | — | T/T |
| chr16 | 23 | C/C | T/C | C/C | T/C | T/C | T/C | T/C | C/C | C/C | C/C |
| chr16 | 24 | A/A | C/A | A/A | A/C | C/A | — | C/A | A/A | A/A | A/A |
| chr16 | 34 | C/C | C/A | C/C | C/A | C/A | C/A | C/A | C/C | C/C | C/C |
| chr16 | 36 | C/C | C/T | C/C | C/T | C/C | T/T | C/T | C/C | C/C | C/C |
| chr16 | 54 | G/G | G/C | G/G | G/G | G/C | G/G | G/G | G/C | G/C | G/G |
| chr16 | 61 | T/T | T/C | T/T | T/C | T/C | T/C | T/C | T/T | T/T | T/T |
| chr16 | 63 | C/C | C/T | C/C | C/T | C/T | C/T | C/T | C/C | C/C | C/C |

There were 11 effective SNPs upstream and downstream of the chr7 breakpoint, and 16 effective SNPs upstream and downstream of the chr16 breakpoint. The SNP genotypes of the father's chr7 and chr16 were haplotyped. Then the maternal haplotype was constructed based on embryos (E2, E4, E5, and E6) with a normal copy number. Specifically, the maternal haplotype was constructed by subtracting the father's homozygous haplotype from the embryos with a normal copy number (E2, E4, E5 and E6). The number of SNPs used for haplotyping was 9-11 on chr7 and 13-16 on chr16 for each embryo. These maternal haplotypes were combined to construct the maternal haplotypes $H_{Achr7}$ and $H_{Bchr7}$ on chr7, and $H_{Achr16}$ and $H_{Bchr16}$ on chr16. The detailed results were shown in Tables 6 and 7.

TABLE 6

Haplotypes upstream and downstream of the chr7 breakpoint in embryos with a normal copy number in this family

| Chromosome | E2 | E4 | E5 | E6 | $H_{Achr7}$ | $H_{Bchr7}$ |
|---|---|---|---|---|---|---|
| chr7 | G | G | G | A | G | A |
| chr7 | A | A | A | C | A | C |
| chr7 | G | G | G | A | G | A |
| chr7 | T | T | T | C | T | C |
| chr7 | C | C | C | T | C | T |
| chr7 | C | C | C | T | C | T |
| chr7 | A | — | A | T | A | T |
| chr7 | G | G | G | A | G | A |
| chr7 | A | A | A | G | A | G |

TABLE 6-continued

Haplotypes upstream and downstream of the chr7 breakpoint in embryos with a normal copy number in this family

| Chromosome | E2 | E4 | E5 | E6 | $H_{Achr7}$ | $H_{Bchr7}$ |
|---|---|---|---|---|---|---|
| chr7 | G | G | G | A | G | A |
| chr7 | T | — | T | C | T | C |
| Number of SNPs on chr7 available for haplotype analysis | 11 | 9 | 11 | 11 | — | — |

TABLE 7

Haplotypes upstream and downstream of the chr16 breakpoint in embryos with a normal copy number in this family

| Chromosome | E2 | E4 | E5 | E6 | $H_{Achr16}$ | $H_{Bchr16}$ |
|---|---|---|---|---|---|---|
| chr16 | T | T | T | C | T | C |
| chr16 | T | T | T | C | T | C |
| chr16 | — | — | T | C | T | C |
| chr16 | G | G | G | A | G | A |
| chr16 | A | A | A | C | A | C |
| chr16 | C | C | C | T | C | T |
| chr16 | C | C | C | T | C | T |
| chr16 | A | — | A | T | A | T |
| chr16 | C | C | C | T | C | T |
| chr16 | T | T | T | C | T | C |
| chr16 | C | — | C | A | C | A |
| chr16 | A | A | A | C | A | C |
| chr16 | T | T | T | C | T | C |

TABLE 7-continued

Haplotypes upstream and downstream of the chr16 breakpoint in embryos with a normal copy number in this family

| Chromosome | E2 | E4 | E5 | E6 | $H_{Achr16}$ | $H_{Bchr16}$ |
|---|---|---|---|---|---|---|
| chr16 | G | G | G | C | G | C |
| chr16 | C | C | C | T | C | T |
| chr16 | T | T | T | C | T | C |
| Number of SNPs on chr16 available for haplotype analysis | 15 | 13 | 16 | 16 | — | — |

In the same way, the embryos (E1, E3, E7, and E8) with CNV were haplotyped. For each embryo, the haplotypes on chr7/chr16 might be determined as normal or translocation-carrying. The results of 4 embryos were mutually verified and comprehensive determination results were obtained. The results were shown in Tables 8 and 9.

TABLE 8

Determination results of haplotypes upstream and downstream of the chr7 breakpoint in embryos with an abnormal copy number in this family

| | E1 | | E3 | | E7 | | E8 | | Comprehensive determination results | |
|---|---|---|---|---|---|---|---|---|---|---|
| Chromosome | Normal | Carrier | Normal | Carrier | Normal | Carrier | Normal | Carrier | Normal | Carrier |
| chr7 | G | A | N/A | N/A | N/A | N/A | N/A | N/A | G | A |
| chr7 | A | C | N/A | N/A | N/A | N/A | N/A | N/A | A | C |
| chr7 | G | A | N/A | N/A | N/A | N/A | N/A | N/A | G | A |
| chr7 | T | C | N/A | N/A | N/A | N/A | N/A | N/A | T | C |
| chr7 | C | T | N/A | N/A | N/A | N/A | N/A | N/A | C | T |
| chr7 | C | T | N/A | N/A | N/A | N/A | N/A | N/A | C | T |
| chr7 | N/A | N/A | A | T | A | T | A | T | A | T |
| chr7 | N/A | N/A | G | A | G | A | G | A | G | A |
| chr7 | N/A | N/A | A | G | A | G | A | G | A | G |
| chr7 | N/A | N/A | G | A | G | A | G | A | G | A |
| chr7 | N/A | N/A | T | C | T | C | T | C | T | C |

"N/A" indicates that the locus was not available for linkage analysis, and the subsequent tables have the same indication method.

TABLE 9

Determination results of haplotypes upstream and downstream of the chr16 breakpoint in embryos with an abnormal copy number in this family

| | E1 | | E3 | | E7 | | E8 | | Comprehensive determination results | |
|---|---|---|---|---|---|---|---|---|---|---|
| Chromosome | Normal | Carrier | Normal | Carrier | Normal | Carrier | Normal | Carrier | Normal | Carrier |
| chr16 | N/A | N/A | T | C | T | C | T | C | T | C |
| chr16 | N/A | N/A | T | C | T | C | T | C | T | C |
| chr16 | N/A | N/A | T | C | — | — | T | C | T | C |
| chr16 | N/A | N/A | G | A | G | A | G | A | G | A |
| chr16 | N/A | N/A | A | C | A | C | A | C | A | C |
| chr16 | N/A | N/A | C | T | C | T | C | T | C | T |
| chr16 | N/A | N/A | C | T | C | T | C | T | C | T |
| chr16 | N/A | N/A | A | T | A | T | A | T | A | T |
| chr16 | N/A | N/A | C | T | C | T | C | T | C | T |
| chr16 | N/A | N/A | T | C | T | C | T | C | T | C |
| chr16 | N/A | N/A | C | A | C | A | C | A | C | A |
| chr16 | A | C | N/A | N/A | N/A | N/A | N/A | N/A | A | C |
| chr16 | T | C | N/A | N/A | N/A | N/A | N/A | N/A | T | C |
| chr16 | G | C | N/A | N/A | N/A | N/A | N/A | N/A | G | C |
| chr16 | C | T | N/A | N/A | N/A | N/A | N/A | N/A | C | T |
| chr16 | T | C | N/A | N/A | N/A | N/A | N/A | N/A | T | C |

Which haplotype represented "normal" and which haplotype represented "translocation-carrying" were determined by comparing the comprehensive identification results with the haplotyping results of $H_{Achr7}$, $H_{Bchr7}$, $H_{Achr16}$ and $H_{Bchr16}$. As shown in Table 10, from the results of 4 abnormal embryos, it was consistently determined that $H_{Achr7}$ was a normal haplotype, and $H_{Bchr7}$ was a translocation-carrying haplotype; and likewise, $H_{Achr16}$ was determined to be a normal haplotype, and $H_{Bchr16}$ to be a translocation-carrying haplotype.

TABLE 10

Haplotyping results of the family

| | Chromosome | | | |
| --- | --- | --- | --- | --- |
| | chr7 | | chr16 | |
| Embryo | $H_{Achr7}$ | $H_{Bchr7}$ | $H_{Achr16}$ | $H_{Bchr16}$ |
| E1 | Normal | Carrier | Normal | Carrier |
| E3 | Normal | Carrier | Normal | Carrier |
| E7 | Normal | Carrier | Normal | Carrier |
| E8 | Normal | Carrier | Normal | Carrier |

(4') Determination of the Carrying Status of Embryos

According to the haplotyping results obtained from the above steps, the carrying status was determined in embryos (E2, E4, E5 and E6) with a normal copy number. The determination results were shown in Table 11. The results showed that embryos E2, E4, and E5 were all normal embryos (without translocation). One normal embryo (without translocation) was selected out by the method of the present application, and so far the identification process was completed. After the embryo was implanted, the pregnant woman normally conceived, and it was confirmed by the amniotic fluid puncture test that the fetal karyotype was normal.

TABLE 11

Determination results of the carrying
status in embryos of this family

| | Chromosome | |
| --- | --- | --- |
| Embryo | chr7 | chr16 |
| E2 | Normal | Normal |
| E4 | Normal | Normal |
| E5 | Normal | Normal |
| E6 | Carrier | Carrier |

The applicant states that detailed methods of the present application are demonstrated in the present application through the above embodiments, however, the present application is not limited to the above detailed methods, and does not mean that the present application must rely on the above detailed methods to implement. It should be apparent to those skilled in the art that, for any improvement of the present application, the equivalent replacement of the raw materials of the present application, the addition of auxiliary components, and the selection of specific modes, etc., will all fall within the protection scope and the disclosure scope of the present application.

What is claimed is:

1. A method for determining a balanced translocation-carrying status in embryos, selecting out a normal embryo without carrying a balanced translocation, and implanting the normal embryo to a woman to conceive a fetus having normal karyotype, wherein the balanced translocation-carrying status in an embryo is determined using the following steps:

(1') identifying the balanced translocation breakpoint in the embryo comprising (i) obtaining DNAs from parents, and samples to be tested from multiple embryos originated from the parents and when the embryos develop to the blastomere or blastocyst stage;

(ii) amplifying the sample to be tested, and constructing a library followed by sequencing, wherein the sequencing is performed by using a high throughput sequencing platform;

the sequencing is single-end sequencing;

the sequencing is performed at a sequencing read length of no less than 30 bp; and the sequencing is performed at a sequencing depth of no less than 0.1 times of the genome;

(iii) aligning genome sequencing reads obtained in step (ii) to a reference genome to obtain position information of the genome sequencing reads aligned on the reference genome, wherein the reference genome is a whole genome, or a part of the whole genome, covering 50% to 95% of the whole genome;

(iv) dividing the reference genome into N region segments, each of which is taken as a window, and the window has a length of $1 \times 10^2$-$1 \times 10^6$ bp, and calculating the copy number of each window;

(v) determining the threshold range of the normal copy numbers, wherein the threshold range of the normal copy numbers is between N'−σ and N'+σ, wherein N' is the ploidy of the sample to be tested, and σ is 0.05-0.2; or the threshold range of the normal copy numbers is between N'−m×SD and N'+m×SD, wherein N' is the ploidy of the sample to be tested, m is any integer from 1 to 3, and SD is the standard deviation of the copy numbers of all windows of the sample to be tested;

calculating the trimean $M_i$ of the copy numbers of each window and its surrounding windows window-by-window, wherein the number of the surrounding windows is from 10 to 100, and the trimean is calculated according to the following formula: $M=Q1/4+M_d/2+Q3/4$, wherein Q1 is the lower quartile, $M_d$ is the median, and Q3 is the upper quartile;

recording the windows with a $M_i$ that does not fall within the threshold range, and combining successive windows until a normal window is encountered;

(vi) defining the successive windows as described in step (v) as a level 1 region, and further calculating the trimean $M_{nps}$ of each window in the level 1 region and surrounding windows, wherein the number of the surrounding windows is from 3 to 10, and the trimean is calculated according to the following formula: $M=Q1/4+M_d/2+Q3/4$, wherein Q1 is the lower quartile, $M_d$ is the median, and Q3 is the upper quartile, wherein the first window is recorded as the first breakpoint $bp_1$ and the normal and abnormal transition window is recorded as breakpoint $bp_i$, wherein the normal and abnormal transition window is determined as follows: defining the first window as the first breakpoint $bp_1$; calculating each window one-by-one, and recording the window as the second breakpoint bp2 when at least two consecutive $M_{nps}$ fall within an abnormal range; go on scanning until at least two consecutive $M_{nps}$ return to the normal range, and recording the window as the third breakpoint $bp_3$, thus in this way, each time a normal and abnormal transition window is encountered, a breakpoint $bp_i$ is recorded until the last window of the level 1 region;

(vii) defining the region between two breakpoints as a level 2 region, and further calculating the trimean $M_j$ of each window in the level 2 region, and the trimean is calculated according to the following formula: $M=Q1/4+M_d/2+Q3/4$, wherein Q1 is the lower quartile, $M_d$ is the median, and Q3 is the upper quartile, wherein the window with a $M_j$ that falls outside the threshold range is the precise copy number variation region, and the start and end positions of the region are the start and end breakpoints of the copy number variation; and (viii) selecting multiple embryos with an abnormal copy number, calculating the balanced translocation breakpoints on two chromosomes in each embryo by using steps (i)-(vii), and calculating the trimean of the balanced translocation breakpoints on the two chromosomes, respectively, which is the precise balanced translocation breakpoints in the embryo;

wherein i in "$M_i$", "$bp_i$" and j in "$M_j$" are independently any positive integer from 1 to N;

(2') detecting SNPs around the breakpoint, wherein the length around the breakpoint is $2 \times 10^5$-$5 \times 10^6$ bp and the number of SNPs is from 10 to 500;

(3') embryo haplotype analysis: selecting effective SNPs, wherein the effective SNP is homozygous in one parent and heterozygous in the other parent; haplotyping one parent according to the SNP genotypes thereof, and constructing the haplotype of the other parent by reference to the embryos having a normal copy number;

(4') haplotyping the embryos having an abnormal copy number, and then classifying the haplotypes into translocation-carrying and non-translocation-carrying ones to determine the haplotyping results; and (5') determination of the carrying status of the embryos: haplotyping the embryos having a normal copy number, and then comparing with the haplotyping results as described in step (4') to determine the translocation-carrying status in the embryos;

after determining the balanced translocation-carrying status in the embryos, a normal embryo without carrying the balanced translocation is selected out and implanted to a woman to conceive a fetus having normal karyotype.

2. The method according to claim 1, wherein in step (2') said detecting SNPs around the breakpoints is performed by using any one method of the group consisting of designing probe array and performing target sequencing, designing primers and subjecting the amplicon to first generation sequencing, and designing primers and subjecting the amplicon to next generation sequencing, or a combination of at least two thereof.

3. The method according to claim 1, wherein:

(iv) of step (1') is dividing the reference genome into N region segments, each of which is taken as a window, and the window has a length of 50000 bp, and calculating the copy number of each window;

(v) of step (1') is determining the threshold range of the normal copy numbers, wherein the threshold range of the normal copy numbers is between $N'-\sigma$ and $N'+\sigma$, wherein N' is the ploidy of the sample to be tested, and $\sigma$ is 0.05-0.2; or the threshold range of the normal copy numbers is between $N'-m \times SD$ and $N'+m \times SD$, wherein N' is the ploidy of the sample to be tested, m is any integer from 1 to 3, and SD is the standard deviation of the copy numbers of all windows of the sample to be tested;

calculating the trimean $M_i$ of the copy numbers of each window and its surrounding windows window-by-window, wherein the number of the surrounding windows is 10, and the trimean is calculated according to the following formula: $M=Q1/4+M_d/2+Q3/4$, wherein Q1 is the lower quartile, $M_d$ is the median, and Q3 is the upper quartile;

recording the windows with a $M_i$ that does not fall within the threshold range, and combining successive windows until a normal window is encountered;

(vi) of step (1') is defining the successive windows as described in step (v) as a level 1 region, and further calculating the trimean $M_{nps}$ of each window in the level 1 region and surrounding windows, wherein the number of the surrounding windows is 3, wherein the first window is recorded as the first breakpoint $bp_1$ and the normal and abnormal transition window is recorded as breakpoint $bp_i$, wherein the normal and abnormal transition window is determined as follows: defining the first window as the first breakpoint $bp_1$; calculating each window one-by-one, and recording the window as the second breakpoint bp2 when at least two consecutive $M_{nps}$ fall within an abnormal range; go on scanning until at least two consecutive $M_{nps}$ return to the normal range, and recording the window as the third breakpoint $bp_3$, thus in this way, each time a normal and abnormal transition window is encountered, a breakpoint $bp_i$ is recorded until the last window of the level 1 region; and step (2') is detecting SNPs around the breakpoint, wherein the length around the breakpoint is $1 \times 10^6$ bp and the number of SNPs is from 10 to 500.

4. The method according to claim 1 wherein the (iv) of step (1') further comprises a step of correcting the copy number of each window and calculating the corrected copy number of each window.

5. The method according to claim 1, wherein the sample to be tested in (i) of step (1') is a biopsy cell of the embryo.

6. The method according to claim 5, wherein the biopsy cell is an ectodermal cell collected from the embryo when it develops to the blastomere or blastocyst stage.

7. The method according to claim 1, wherein the amplification in (ii) of step (1') is a single cell amplification.

8. The method according to claim 7, wherein the single cell amplification is performed by any one of the group consisting of Primer Extension Preamplification PCR, Degenerate Oligonucleotide Primer PCR, Multiple Displacement Amplification, and Multiple Annealing and Looping Based Amplification Cycles, or a combination of at least two thereof.

* * * * *